US008822537B2

(12) United States Patent
Buyuktimkin et al.

(10) Patent No.: US 8,822,537 B2
(45) Date of Patent: Sep. 2, 2014

(54) TOPICAL KETOPROFEN COMPOSITION

(71) Applicant: Achelios Therapeutics, Inc., Chapel Hill, NC (US)

(72) Inventors: Servet Buyuktimkin, San Diego, CA (US); Nadir Buyuktimkin, San Diego, CA (US); James L. Yeager, Lake Forest, IL (US)

(73) Assignee: Achelios Therapeutics, Inc., Chapel Hill, NC (US)

( * ) Notice: Subject to any disclaimer, the term of this patent is extended or adjusted under 35 U.S.C. 154(b) by 0 days.

(21) Appl. No.: 13/826,706

(22) Filed: Mar. 14, 2013

(65) Prior Publication Data

US 2014/0088195 A1    Mar. 27, 2014

Related U.S. Application Data

(60) Provisional application No. 61/706,163, filed on Sep. 27, 2012.

(51) Int. Cl.
*A61K 31/19*    (2006.01)

(52) U.S. Cl.
USPC .......................................................... 514/557

(58) Field of Classification Search
USPC .......................................................... 514/557
See application file for complete search history.

(56) References Cited

U.S. PATENT DOCUMENTS

| 6,613,341 | B2 * | 9/2003 | Motley et al. | 424/401 |
| 8,367,701 | B2 * | 2/2013 | Burnier et al. | 514/307 |
| 8,409,600 | B2 * | 4/2013 | Friedman et al. | 424/423 |

* cited by examiner

*Primary Examiner* — Zohreh Fay
(74) *Attorney, Agent, or Firm* — Olson & Cepuritis, Ltd.

(57) ABSTRACT

A topical composition, specifically an oil-in-water emulsion, comprised of ketoprofen and oxybenzone in a physiologically acceptable topical carrier. The composition is applied topically to alleviate pain, especially pain associated with migraine headache. The composition has good photostability as well as freeze/thaw stability.

10 Claims, 14 Drawing Sheets
(14 of 14 Drawing Sheet(s) Filed in Color)

TOPICAL KETOPROFEN COMPOSITION

CROSS-REFERENCE TO RELATED APPLICATION

This application claims the benefit of U.S. Provisional Application No. 61/706,163, filed on Sep. 27, 2012, which is incorporated herein by reference in its entirety.

FIELD OF THE INVENTION

This invention relates generally to a non-irritating topical analgesic composition for the treatment of pain such as nociceptive pain, inflammatory pain, pathological pain, as well as for the treatment of migraine pain.

BACKGROUND OF THE INVENTION

Pain is a major symptom in many medical conditions, and can significantly interfere with a person's quality of life and general functioning. Three categories of pain are generally recognized: nociceptive pain which is caused by stimulation of peripheral nerve fibers; inflammatory pain which is associated with tissue damage and the infiltration of immune cells; and pathological pain which is a disease state caused by damage to the nervous system or by its abnormal function (dysfunctional pain, like in fibromyalgia, irritable bowel syndrome, tension type headache, etc.). Acute pain is usually managed with medications such as analgesics and anesthetics.

A migraine headache is a chronic disorder characterized by moderate to severe headaches and nausea. It is believed to be a neurovascular disorder. Migraines typically present with recurrent severe headache associated with autonomic symptoms. The typical migraine headache is unilateral, throbbing, and moderate to severe, and can be aggravated by physical activity Initial treatment is with analgesics for the headache, an antiemetic for the nausea, and the avoidance of triggers. A number of analgesics are effective for treating migraines including: non-steroidal anti-inflammatory drugs (NSAIDs); paracetamol/acetaminophen; and simple analgesics combined with caffeine.

NSAIDs provide analgesic and antipyretic (fever-reducing) effects, and, in higher doses, anti-inflammatory effects. The term "nonsteroidal" distinguishes these drugs from steroids, which, among a broad range of other effects, have a similar eicosanoid-depressing, anti-inflammatory action. As analgesics, NSAIDs are unusual in that they are non-narcotic. NSAIDs are usually indicated for the treatment of acute or chronic conditions where pain and inflammation are present. The widespread use of NSAIDs has meant that the adverse effects of these drugs have become increasingly prevalent. The two main adverse drug reactions associated with NSAIDs relate to gastrointestinal effects and renal effects of the agents.

NSAIDs can be classified based on their chemical structure or mechanism of action. Common NSAID classification groups include: Salicylates, Propionic acid derivatives, Acetic acid derivatives, Enolic acid derivatives, Fenamic acid derivatives, Selective COX-2 inhibitors, and Sulphonanilides. NSAIDs within a group tend to have similar characteristics and tolerability. There is little difference in clinical efficacy among the NSAIDs when used at equivalent doses. Rather, differences among compounds usually relate to dosing regimens, route of administration, and tolerability profile.

Ketoprofen is a nonsteroidal anti inflammatory proprionic acid derivative. It has potent anti inflammatory and analgesic activity. Conventionally, ketoprofen and other related drugs have been administered orally; however, they have been accompanied by systemic side effects or gastrointestinal irritation. In order to reduce these side effects, these drugs have been formulated as transdermal preparations. The skin permeability of these NSAIDs is known to be higher than other NSAIDs.

To minimize the foregoing drawbacks, attempts have been made to develop topical ketoprofen compositions. These attempts have been met with limited success due to photosensitivity and stability problems as well as photoallergy potential.

SUMMARY OF THE INVENTION

The present invention provides a topical NSAID composition for alleviating pain associated with conditions such as migraine headache, which is stable under intense ultraviolet (UV) light as well as in freeze-thaw conditions. The composition comprises ketoprofen in a physiologically acceptable carrier formulated into a topical cream. The composition has relatively high skin permeability, is chemically and physically stable, as well as photostable.

The compositions embodying the present invention contain, on a weight basis, about 0.5 to about 15 percent ketoprofen, about 0.01 to about 1 percent of a chelating agent, about 0.15 to about 1.5 percent of a cross-linked polyacrylic acid homopolymer, about 0.15 to about 1.5 percent of a cross-linked polyacrylic acid interpolymer, about 2.5 to about 6 percent oxybenzone, about 0.25 to about 2.5 percent of a an emulsifying agent, about 5 to about 15 percent of a water-miscible alkylene glycol, about 10 to about 30 percent of a $C_2$ to $C_3$ alkanol, about 0.5 to about 2.5 percent of a cosmetic preservative, about 0.02 to about 2 percent of an antioxidant, about 0.001 to about 0.1 percent of an emollient, a pH modifier in an amount sufficient to maintain a pH value in the range of about 4.5 to about 6, and the remainder, water.

The pH value of the foregoing compositions is in the range of about 4.5 to about 6, preferably about 5. The total amount of the glycols and polyhydric alcohols and monohydric alcohols present does not exceed about 35 weight percent.

BRIEF DESCRIPTION OF THE DRAWINGS

The patent or application file contains drawings executed in color. Copies of this patent or patent application publication with color drawings will be provided by the U.S. Patent and Trademark Office upon request and payment of the necessary fee.

In the Drawings.

DETAILED DESCRIPTION OF PREFERRED EMBODIMENTS

Figure 1:
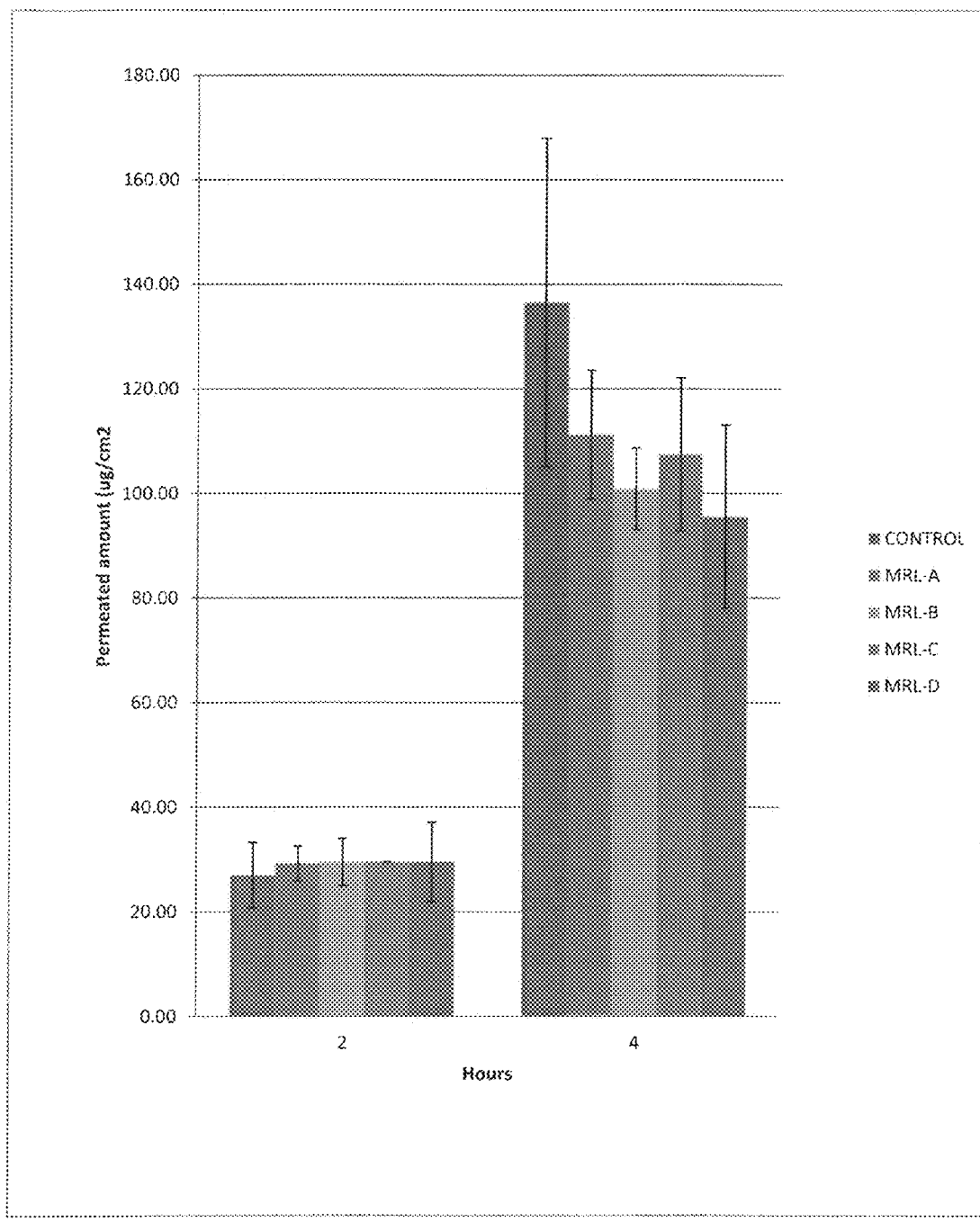
FIG. 1 is a histogram showing permeated amount of ketoprofen permeated two hours and four hours after application of compositions shown in Table 2.

The composition of the present invention is an oil-in-water emulsion comprising the active ingredient ketoprofen in an amount in the range of about 0.5 to about 15 weight percent, preferably about 10 weight percent. The oil-in-water emulsion is a viscous liquid or semi-solid having a cream-like consistency. Viscosity can vary over a relatively wide range, usually about 2,000 centipoises to about 60,000 centipoises.

Ketoprofen, molecular formula $C_{16}H_{14}O_3$, is one of the propionic acid class of NSAIDs with both analgesic and antipyretic effects. It acts by inhibiting the body's production of prostaglandin. Ketoprofen inhibits cyclooxygenase-1 and -2 (COX-1 and COX-2) enzymes reversibly, which in turn, decreases production of proinflammatory prostaglandin precursors.

Edetate disodium is also known as the disodium salt of ethylenediaminetetraacetic acid (EDTA). EDTA is available in several salt forms, notably disodium EDTA and calcium disodium EDTA. EDTA is mainly used to sequester metal ions in aqueous solution. In personal care products, it is added to cosmetics to improve their stability toward air. It acts as a chelating agent that helps bind free radicals and impurities in the present composition.

The cross-linked polyacrylic acid polymers present serve as thickners and also provide freeze-thaw stability for the composition. A cross-linked polyacrylic acid homopolymer suitable for present purposes is a high molecular weight polymer of acrylic acid cross-linked with polyalkenyl ethers of sugars or polyalcohols such as allyl sucrose, allyl pentaerythritol, etc., such as Carbopol® 980 NF, and the like. Carbopol® 980 NF is commercially available from Lubrizol Advanced Materials, Inc., Cleveland, Ohio. A cross-linked polyacrylic acid interpolymer suitable for present purposes is a high molecular weight copolymer of acrylic acid and $C_1$-$C_{24}$ alkylmethacrylates cross-linked with polyalkenyl ethers of sugars or polyalcohols which contain a heterologous polymer, e.g., a block copolymer of polyethylene glycol and a long chain, e.g., $C_1$-$C_{24}$ alkyl acid esters, such as Carbopol® Ultrez 10 NF, and the like. Carbopol® Ultrez 10 NF is commercially available from Lubrizol Advanced Materials, Inc., Cleveland, Ohio. For optimum free-thaw stability, the interpolymer-homopolymer weight ratio in the composition is about 2.5:1.

PEG-40 hydrogenated castor oil is a polyethylene glycol derivative of castor oil. In the present composition it acts as an emulsifying agent. It also aids the dissolution of ingredients in a solvent in which they would not normally dissolve.

Vitamin E refers to a group of eight fat-soluble compounds that include both tocopherols and tocotrienols. Vitamin E has many biological functions; the antioxidant function being the most important and best known. It acts as such in the present compositions.

Suitable water-miscible alkylene glycols are the polyhydric alcohols such as glycerol, dipropylene glycol, polyethylene glycol, propylene carbonate, propylene glycol, butylene glycol, pentylene glycol, hexylene glycol, and the like. Propylene glycol is the preferred water-miscible alkylene glycol.

Propylene glycol is a colorless, nearly odorless, clear, viscous liquid. Propylene glycol acts as a solvent and antimicrobial in the present formulation. The freezing point of water is depressed when mixed with propylene glycol due to increased opportunity for hydrogen bonding.

Suitable monohydric alkanol alcohols are the $C_2$ and $C_3$ alkanols such as ethanol, propanol, isopropanol, and the like. Isopropyl alcohol is the preferred alcohol.

Isopropyl alcohol is a colorless, flammable, chemical compound. It is miscible in water, alcohol, ether and chloroform. Isopropyl alcohol dissolves a wide range of non-polar compounds. It also evaporates quickly and is relatively non-toxic, compared to alternative solvents. In the present composition, isopropyl alcohol acts as a solvent and permeation enhancer.

Suitable emollients are isopropyl myristate, isopropyl palmitate, lanolin, and the like. Isopropyl myristate is the preferred emollient.

Isopropyl myristate acts as a solvent, stabilizer, as well as an emollient in the present composition.

Suitable cosmetic preservatives are the parabens such as methylparaben, propylparaben, butylparaben, phenol derivatives such as phenoxyethanol, benzyl alcohol, and the like. Benzyl alcohol is the preferred preservatives.

Benzyl alcohol is partially soluble in water and completely miscible in alcohols and diethyl ether. Benzyl alcohol acts as a bacteriostatic preservative in the present compositions.

Oxybenzone, molecular formula $C_{14}H_{12}O_3$, absorbs UVB and UVA (ultraviolet) radiation. It forms colorless crystals that a readily soluble in most organic solvents and contributes to the photostability of the composition.

Butylated hydroxytoluene (BHT) is a lipophilic organic compound, chemically a derivative of phenol. It acts as an antioxidant and antimicrobial compound in the present formulation.

Triethanolamine is an organic compound that is both a tertiary amine and a triol. Like other amines, triethanolamine is a strong base and functions as a pH modifier in the present composition. Triethanolamine is used primarily as an emulsifier and surfactant. Triethanolamine neutralizes fatty acids, adjusts and buffers the pH, and solubilizes oils and other ingredients that are not fully soluble in water.

The alcohols present in the compositions contribute to skin permeation; however, the total alcohol concentration should not exceed 30% w/w to maintain optimum skin permeation. The total propylene glycol concentration should not exceed 10% w/w to avoid a negative effect on permeation and physical stability.

Optionally a plant derived protein, such as soy protein and the like, or an animal derived protein such as bovine serum albumin (BSA), and the like, can be added to the present compositions as solubility enhancers, if desired.

Table 1 lists the components of preferred compositions containing a 10 percent by weight ketoprofen, 5 percent by weight ketoprofen, and 0.5 percent by weight ketoprofen.

TABLE 1

| Component | w/w % | | |
|---|---|---|---|
| Ketoprofen, USP | 10 | 5 | 0.5 |
| Disodium EDTA, USP | 0.05 | 0.05 | 0.05 |
| Purified Water, USP | q.s. | q.s. | q.s. |
| Carbopol ® 980, NF | 0.5 | 0.5 | 0.5 |
| Carbopol ® Ultrez 10, NF | 1.25 | 1.25 | 1.25 |
| PEG-40 Hydrogenated Castor Oil, NF | 0.5 | 0.5 | 0.5 |
| Vitamin E USP | 0.05 | 0.05 | 0.05 |
| Ethyl Alcohol USP, anhydrous | 10 | 10 | 10 |
| Propylene glycol, USP | 10 | 10 | 10 |
| Isopropanol, USP | 9 | 10 | 10 |
| Isopropyl Myristate, USP | 3 | 3 | 3 |
| Benzyl Alcohol, NF | 1 | 1 | 1 |
| Oxybenzone, USP | 5 | 5 | 5 |
| Butylated Hydroxytoluene, NF | 1 | 1 | 1 |
| Triethanolamine | 1.5 | 1.5 | 1.5 |
| pH | 5 | 5 | 5 |

The preferred compositions have relatively high skin permeation within the first 2 hours and excellent continued permeation for up to 22 hours.

The present invention is illustrated by the following experimental data:

I. Materials and Methods

1. Materials

Ketoprofen was obtained from Boehinger-Ingelheim.

All other materials were obtained from various chemical supply houses.

2. HPLC Analytical Methods for Cream Assay and Permeation Studies

Chromatographic Conditions:

An isocratic reversed-phase HPLC system was used to determine the stability and photostability of the ketoprofen formulations. The HPLC instrument was Agilent 1100. Nova-Pak® 4.6×300 mm C18 column from Waters was used. The mobile phase consisted of a mixture of formic acid buffer (0.025 M) adjusted to pH 2.3 with hydrochloric acid and acetonitrile (50:50). The flow rate was 1.0 ml/min. Detection was accomplished at 220 nm and 254 nm. The volume of injection was set to 25 μl. Under these conditions, the retention times of ketoprofen and oxybenzone were approximately 5 min. and 13 min., respectively. The concentration ranges for the calibration curves of ketoprofen and oxybenzone were 7-210 μg/ml and 120-480 μg/ml, respectively. The run time for the samples was 20 min.

Sample Preparation:

For the stability studies, approximately 75 or 50 mg of sample for compositions containing 5% and 10% ketoprofen, respectively, was weighed directly in 25 ml volumetric flasks. Approximately 20 ml of mobile phase was added to each flask, then vortexed for 3 min., filled to volume with mobile phase and shaken well.

For photostability studies, approximately 150 mg of sample was weighed in procelain crucible which was spread evenly across the bottom of the vessel. The crucibles were passed under a UV curing system (Fusion UV Curing LC6B with H Lamp, Fusion Systems, Rockville, Md.) on a conveyor belt for 5 min. which moved at a speed of 7 to 8 passes per min. The intensity of the UV light was measured using a digital illuminometer (Model YF-1065F) whose value ranged consistently from 250 to 300 foot candles. In comparison, the intensity of light in the laboratory was only 2 to 3 foot candles. The composition in the crucible was then washed 5 times with mobile phase into 150 ml beakers and transferred to 50 ml volumetric flasks with triplicate washings. The flasks were vortexed for 3 min., filled to volume with mobile phase and shaken well. The diluted samples were centrifuged for 10 min. prior to filling the HPLC vials for analysis.

3. Methodology for Assessing the Permeation of Ketoprofen

Dermatomed cadaver skin (Science Care, Aurora, Colo.) was used without further treatment. Porcine skin (Lampire Biological Laboratories, Pipersville, Pa.) was dermatomed to standard thickness. Permeation studies were performed using modified Franz cells with an exposed skin membrane surface area of approximately 1.3 cm$^2$ at 37° C. with sampling times at 2, 4, and 22 hours and assayed by HPLC. Each Franz cell received one small aliquot of cream sample of approximately 100 mg, lightly spread on the skin membrane surface using a glass rod and covered with a cover disc to prevent moisture loss. The receptor phase contained pH 7.4 phosphate buffer.

4. Methodology for Assessing the Photodegradation of Ketoprofen and Oxybenzone

Preparations were exposed to an ultra high intensity UV light source (~300 lux) for 5 minutes or 10 minutes. At this exposure level human skin would readily burn. Aliquots of the exposed cream were assayed for ketoprofen and oxybenzone content using the HPLC procedure described above.

5. Methodology for Assessing Freeze/Thaw Stability

Samples were stored at 0° C. for 24 hours followed by thawing at 25° C. for 24 hours. Samples were observed for phase separation after each cycle. For each sample, five cycles were assessed.

Formulation Research Studies—Permeation of Ketoprofen

1. A series of studies were conducted to find an acceptable stabilizing polymer thickener(s) and find the optimum levels of these polymers that would minimize freeze/thaw failure. These studies are presented below.

a. The effect of selected polymers: Carbopol® 980; Carbopol® Ultrez 10 and Carbopol® Ultrez 20, and their combinations on the permeation of ketoprofen through human cadaver skin.

TABLE 2

| | Composition (% w/w) | | | | |
|---|---|---|---|---|---|
| Ingredient | Control | MRL-A | MRL-B | MRL-C | MRL-D |
| Ketoprofen | 5 | 5 | 5 | 5 | 5 |
| Carbopol ® Ultrez 10 NF | | 1.75 | | 0.75 | |
| Carbopol ® Ultrez 20 | | | 1.75 | | 0.75 |
| Carbopol ® 980 | 1.5 | | | 1 | 1 |
| Deionized Water | 58.73 | 52.15 | 52.15 | 52.15 | 52.15 |
| Disodium EDTA | 0.05 | 0.05 | 0.05 | 0.05 | 0.05 |
| Methylparaben, NF | 0.2 | 0 | 0 | 0 | 0 |
| Propylparaben, NF | 0.02 | 0 | 0 | 0 | 0 |
| Propylene glycol | | 10 | 10 | 10 | 10 |
| Isopropanol | | 10 | 10 | 10 | 10 |
| Cremophor 40[1] | | 0.5 | 0.5 | 0.5 | 0.5 |
| Oxybenzone | | 5 | 5 | 5 | 5 |
| BHT | | 1 | 1 | 1 | 1 |
| Vitamin E | | 0.05 | 0.05 | 0.05 | 0.05 |
| Isopropyl Myristate | 3 | 3 | 3 | 3 | 3 |
| Ethyl Alcohol USP, anh. | 30 | 10 | 10 | 10 | 10 |
| Triethanolamine, NF | 1.5 | 1.5 | 1.5 | 1.5 | 1.5 |

[1]PEG-40, Hydrogenated Castor Oil, NF.

Figure 2:
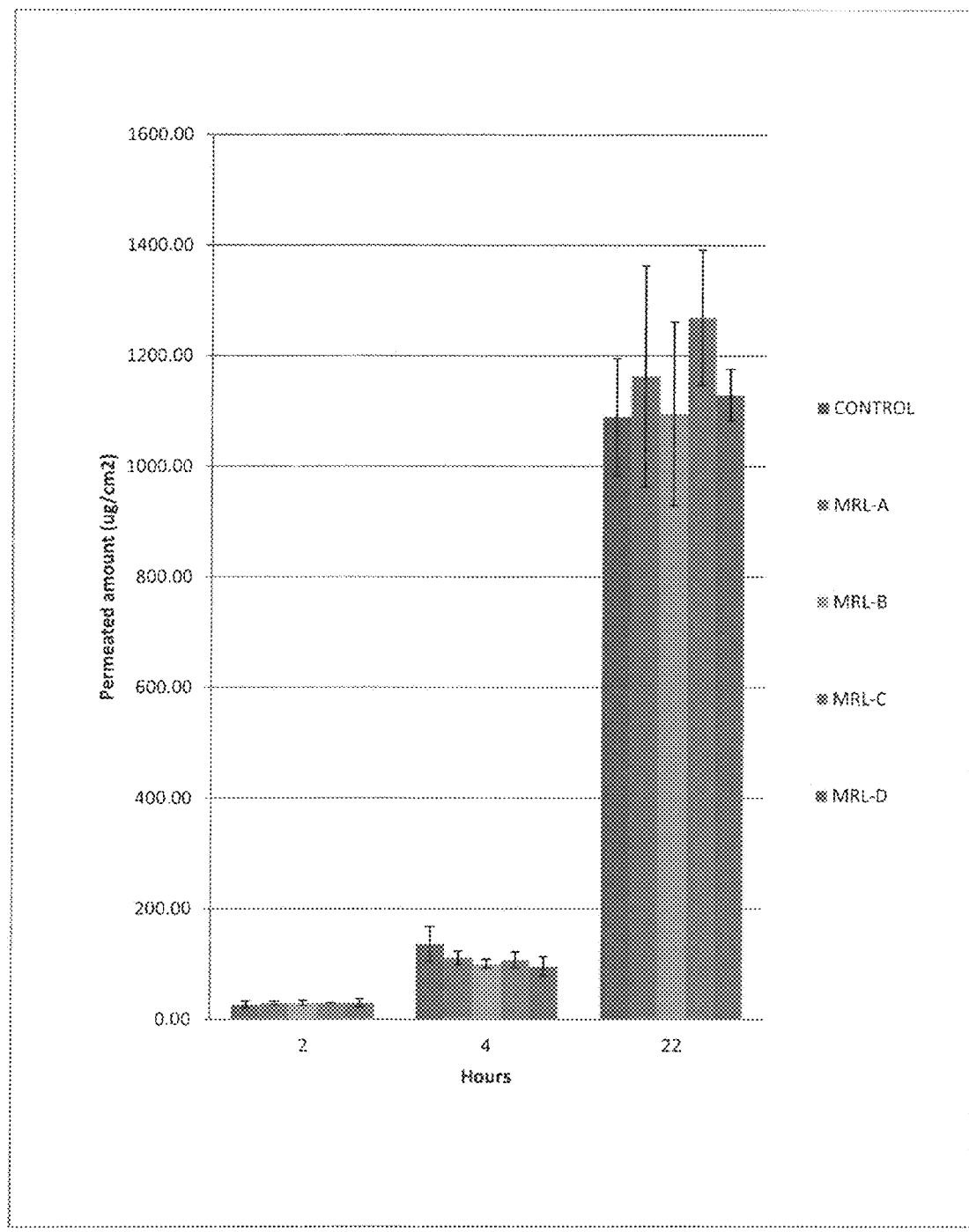
FIG. 2 is a histogram showing amount of ketoprofen permeated two hours, four hours, and 22 hours after application of compositions shown in Table 2.

All of the foregoing preparations showed similar permeation. The observed results are shown in FIGS. 1 and 2.

b. The effect of Carbopol® Ultrez 10 alone at the level of 1.75% w/w on the permeation of ketoprofen through human cadaver skin.

TABLE 3

| | Composition (% w/w) | |
|---|---|---|
| Ingredient | Control | MRL-E |
| Ketoprofen | 5 | 10 |
| Carbopol® Ultrez 10 NF | | 1.75 |
| Carbopol® 980 | 1.5 | |
| Deionized Water | 58.73 | 47.15 |
| Methyl paraben | 0.2 | |
| Propyl paraben | 0.02 | |
| Disodium EDTA | 0.05 | 0.05 |
| Propylene glycol | | 10 |
| Isopropanol | | 9 |
| Cremophor 40[1] | | 0.5 |
| Benzyl alcohol | | 1 |
| Oxybenzone | | 5 |
| BHT | | 1 |
| Vitamin E | | 0.05 |
| Isopropyl Myristate | 3 | 3 |
| Ethyl Alcohol USP, ahn. | 30 | 10 |
| Triethanolamine, NF | 1.5 | 1.5 |

[1]PEG-40 Hydrogenated Castor Oil, NF.

Figure 3:
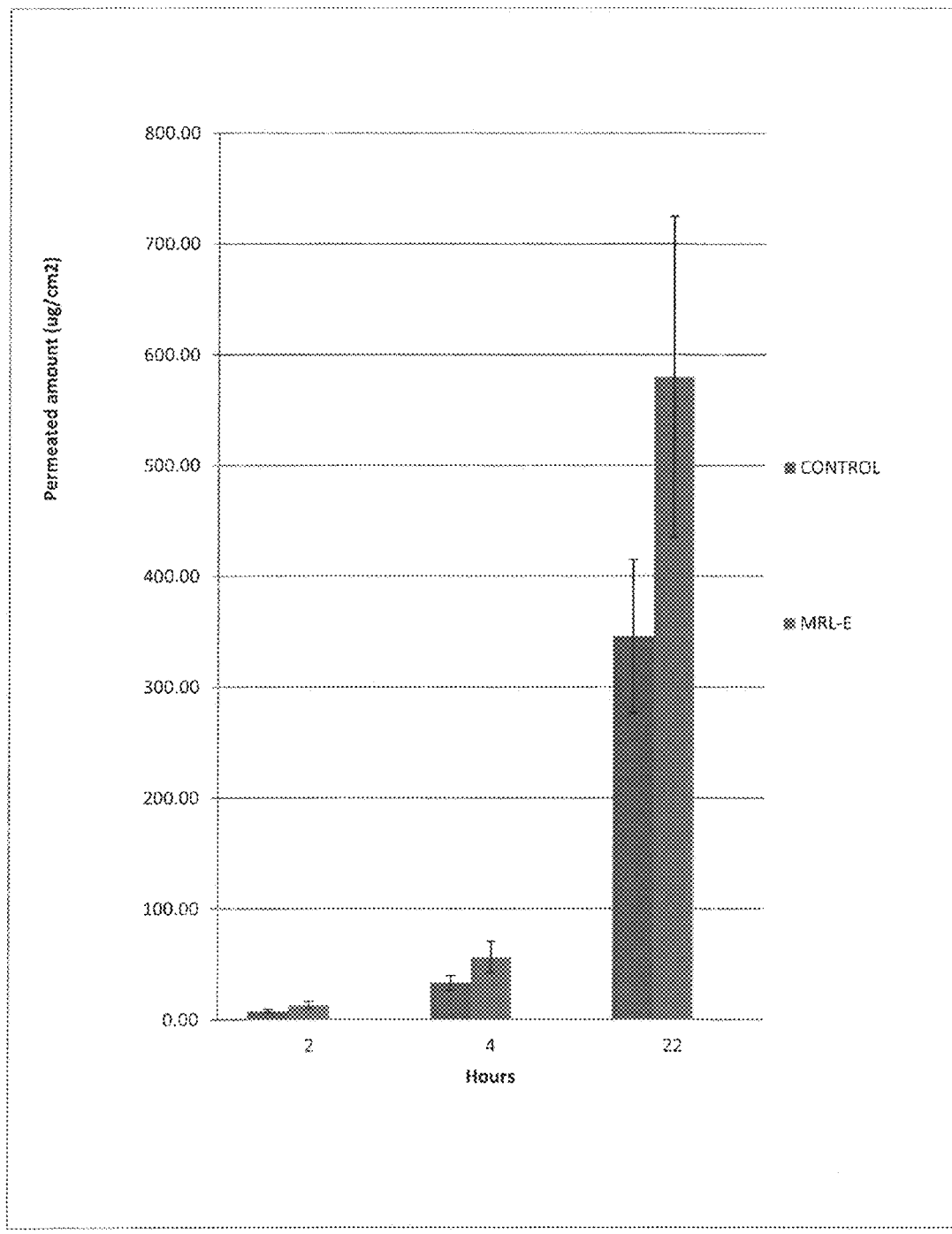
FIG. 3 is a histogram showing amount of ketoprofen permeated two hours, four hours, and 22 hours after application of compositions shown in Table 3.

The foregoing composition containing Ultrez 10 alone at the level of 1.75% exhibited improved permeation after 4 hours and 22 hours. The observed results are shown in FIG. 3.

c. An evaluation of Carbopol® Ultrez 10 and Carbopol® 980 combinations on the permeation of ketoprofen through porcine skin.

TABLE 4

| | Composition (% w/w) | | | |
|---|---|---|---|---|
| Ingredient | Control | MRL-F | MRL-G | MRL-H |
| Ketoprofen | 5 | 10 | 10 | 10 |
| Carbopol® Ultrez 10 NF | | 0.25 | 0.75 | 0.5 |
| Carbopol® 980 | 1.5 | 1.5 | 1 | 1.25 |
| Deionized Water | 58.73 | 46.15 | 46.15 | 46.15 |
| Disodium EDTA | 0.05 | 0.05 | 0.05 | 0.05 |
| Propylene glycol | | 10 | 10 | 10 |
| Isopropanol | | 10 | 10 | 10 |
| Cremophor 40[1] | | 0.5 | 0.5 | 0.5 |
| Benzyl alcohol | | 1 | 1 | 1 |
| Oxybenzone | | 5 | 5 | 5 |
| Methyl paraben | 0.2 | | | |
| Propyl paraben | 0.02 | | | |
| BHT | | 1 | 1 | 1 |
| Vitamin E | | 0.05 | 0.05 | 0.05 |
| Isopropyl Myristate | 3 | 3 | 3 | 3 |
| Ethyl Alcohol USP, anh. | 30 | 10 | 10 | 10 |
| Triethanolamine, NF | 1.5 | 1.5 | 1.5 | 1.5 |

[1]PEG-40 Hydrogenated Castor Oil.

Figure 4:
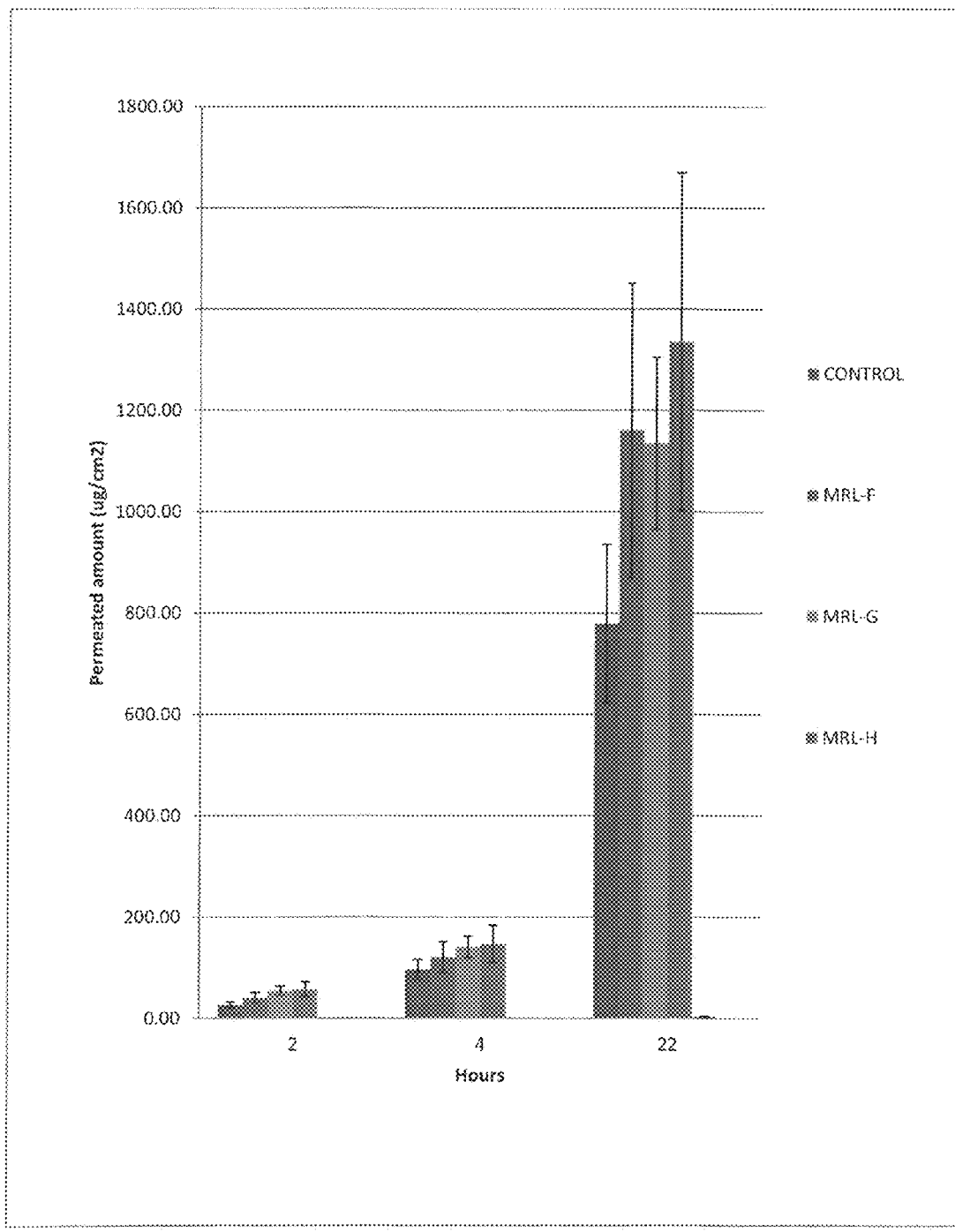
FIG. 4 is a histogram showing amount of ketoprofen permeated two hours, four hours, and 22 hours after application of compositions shown in Table 4.

Carbopol® Ultrez 10 and Carbopol® 980 combinations showed improved permeation compared to the control formulation. The ratio of the two polymers is important for the optimization of ketoprofen permeation. The observed results are shown in FIG. 4.

d. Ketoprofen permeation from larger (kg) batches using the Carbopol® 980/Carbopol® Ultrez 10 ratio of 1%/0.75%.

TABLE 5

| | Composition (% w/w) | | |
|---|---|---|---|
| Ingredient | MRL-I | MRL-J | MRL-K |
| Ketoprofen | 0 | 5 | 10 |
| Carbopol® 980 | 1 | 1 | 1 |
| Carbopol® Ultrez 10 NF | 0.75 | 0.75 | 0.75 |
| Deionized Water | 57.198 | 52.198 | 47.198 |
| Disodium EDTA | 0.05 | 0.05 | 0.05 |
| Propylene glycol | 10 | 10 | 10 |
| Isopropanol | 9 | 9 | 9 |
| Benzyl alcohol | 1 | 1 | 1 |
| Cremophor 40[1] | 0.5 | 0.5 | 0.5 |
| Oxybenzone | 5 | 5 | 5 |
| BHT | 1 | 1 | 1 |
| Vitamin E | 0.002 | 0.002 | 0.002 |
| Isopropyl Myristate | 3 | 3 | 3 |
| Ethyl Alcohol USP, anh. | 10 | 10 | 10 |
| Triethanolamine, NF | 1.5 | 1.5 | 1.5 |

[1]PEG-40 Hydrogenated Castor Oil.

Figure 5:
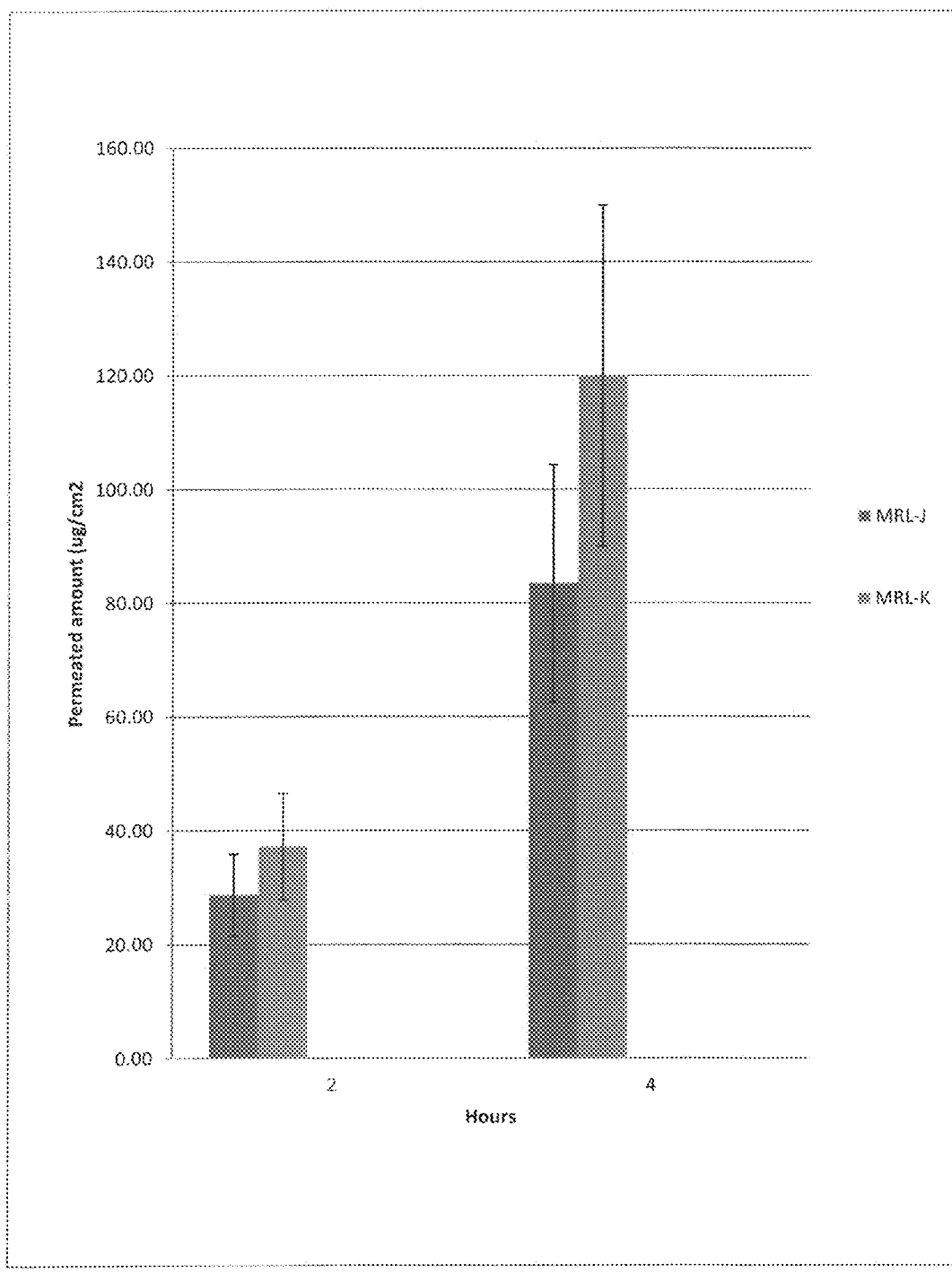
FIG. 5 is a histogram showing amount of ketoprofen permeated two hours, four hours, and 22 hours after application of compositions shown in Table 5.

The 10% cream had higher ketoprofen permeation at all time points. The observed results are shown in FIG. 5.

e. Evaluation of the effect of Carbopol® Ultrez 10/Carbopol® 980 ratios on the permeation of ketoprofen (100 gram batches).

TABLE 6

| | Composition (% w/w) | | |
|---|---|---|---|
| Ingredient | Control | MRL-L | MRL-M |
| Ketoprofen | 5 | 10 | 10 |
| Carbopol® Ultrez 10 NF | | 1.25 | 1.5 |
| Carbopol® 980 | 1.5 | 0.5 | 0.25 |
| Deionized Water | 58.73 | 46.15 | 46.15 |
| Disodium EDTA | 0.05 | 0.05 | 0.05 |
| Propylene glycol | | 10 | 10 |
| Isopropanol | | 10 | 10 |
| Cremophor 40[1] | | 0.5 | 0.5 |
| Methyl paraben | 0.2 | | |
| Propylparaben | 0.02 | | |
| Benzyl alcohol | | 1 | 1 |
| Oxybenzone | | 5 | 5 |
| BHT | | 1 | 1 |
| Vitamin E | | 0.05 | 0.05 |
| Isopropyl Myristate | 3 | 3 | 3 |
| Ethyl Alcohol USP, anh. | 30 | 10 | 10 |
| Triethanolamine, NF | 1.5 | 1.5 | 1.5 |

[1]PEG 40 Hydrogenated Castor Oil.

Figure 6:
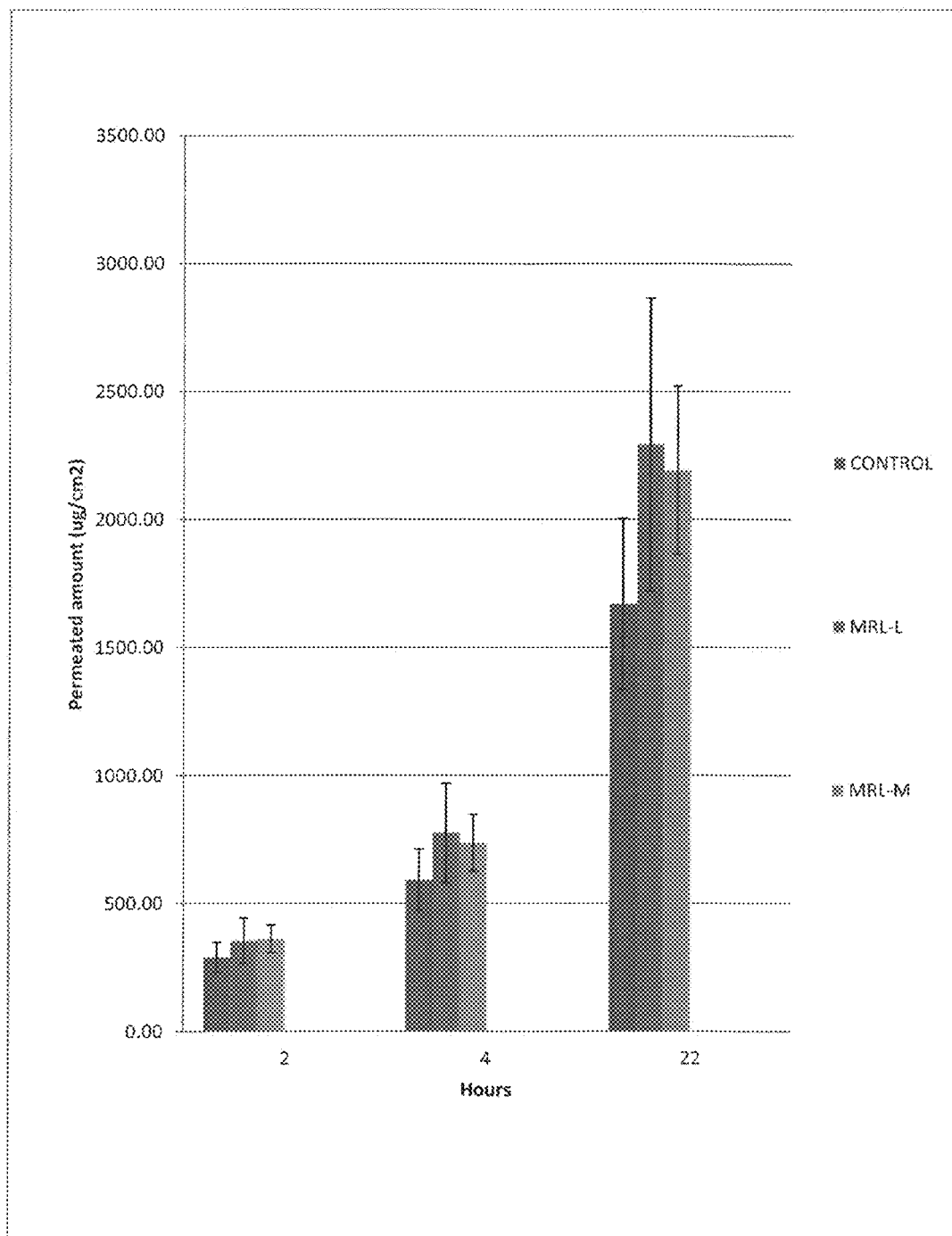
FIG. 6 is a histogram showing amount of ketoprofen permeated two hours, four hours, and 22 hours after application of compositions shown in Table 6.

Good permeation was achieved with all preparations. Data shows that relatively higher amounts of Carbopol® Ultrez 10 result in relatively higher ketoprofen permeation. The observed results are shown in FIG. 6.

The cosmetic appearance of the Carbopol® Ultrez 10 compositions also improves with higher amounts of the polymer present.

f. Ketoprofen permeation from 1 kg batches made with the Carbopol®Ultrez 10/Carbopol® 980 ratio of 1.25%/0.5%.

TABLE 7

| | Composition (% w/w) | | |
|---|---|---|---|
| Ingredient | Control | MRL-N | MRL-O |
| Ketoprofen | 5 | 5 | 10 |
| Carbopol® Ultrez 10 NF | | 1.25 | 1.25 |

TABLE 7-continued

| | Composition (% w/w) | | |
|---|---|---|---|
| Ingredient | Control | MRL-N | MRL-O |
| Carbopol ® 980 | 1.5 | 0.5 | 0.5 |
| Deionized Water | 58.73 | 51.15 | 46.15 |
| Disodium EDTA | 0.05 | 0.05 | 0.05 |
| Propylene glycol | | 10 | 10 |
| Isopropanol | | 10 | 10 |
| Cremophor 40[1] | | 0.5 | 0.5 |
| Benzyl alcohol | | 1 | 1 |
| Methyl paraben | 0.2 | | |
| Propyl paraben | 0.02 | | |
| Oxybenzone | | 5 | 5 |
| BHT | | 1 | 1 |
| Vitamin E | | 0.05 | 0.05 |
| Isopropyl Myristate | 3 | 3 | 3 |
| Ethyl Alcohol USP, anh. | 30 | 10 | 10 |
| Triethanolamine, NF | 1.5 | 1.5 | 1.5 |

[1]PEG 40 Hydrogenated Castor Oil.

Figure 7:
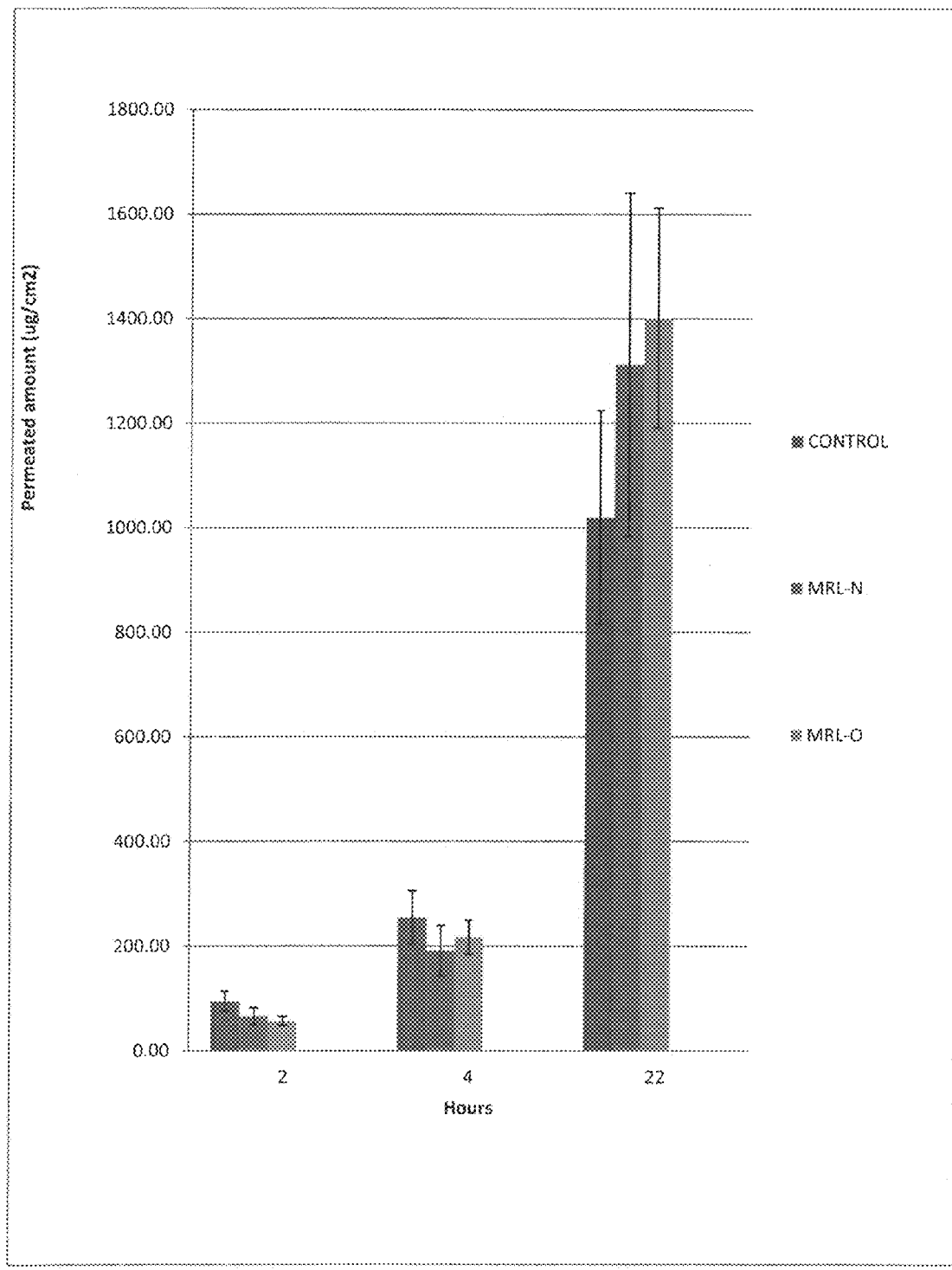
FIG. 7 is a histogram showing amount of ketoprofen permeated two hours, four hours, and 22 hours after application of compositions shown in Table 7.

The permeation results are shown in FIG. 7.

g. Evaluation of the effect of Carbopol® 980 and Carbopol® Ultrez 10 ratios on the permeation of ketoprofen through procine skin.

TABLE 8

| | Composition (% w/w) | | | |
|---|---|---|---|---|
| Ingredient | Control | MRL-P | MRL-Q | MRL-R |
| Ketoprofen | 5 | 10 | 10 | 10 |
| Carbopol ® Ultrez 10 NF | | 1.25 | 1.25 | 1.25 |
| Carbopol ® 980 | 1.5 | 0.75 | 0.5 | 0.75 |
| Deionized Water | 58.73 | 45.9 | 41.15 | 40.9 |
| Disodium EDTA | 0.05 | 0.05 | 0.05 | 0.05 |
| Propylene glycol | | 10 | 10 | 10 |
| Isopropanol | | 10 | 10 | 10 |
| Cremophor 40[1] | | 0.5 | 0.5 | 0.5 |
| Benzyl alcohol | | 1 | 1 | 1 |
| Methyl paraben | 0.2 | | | |
| Propylparaben | 0.02 | | | |
| Oxybenzone | | 5 | 5 | 5 |
| BHT | | 1 | 1 | 1 |
| Vitamin E | | 0.05 | 0.05 | 0.05 |
| Isopropyl Myristate | 3 | 3 | 3 | 3 |
| Ethyl Alcohol USP, anh. | 30 | 10 | 15 | 15 |
| Triethanolamine, NF | 1.5 | 1.5 | 1.5 | 1.5 |

[1]PEG 40 to Hydrogenated Castor Oil.

Figure 8:
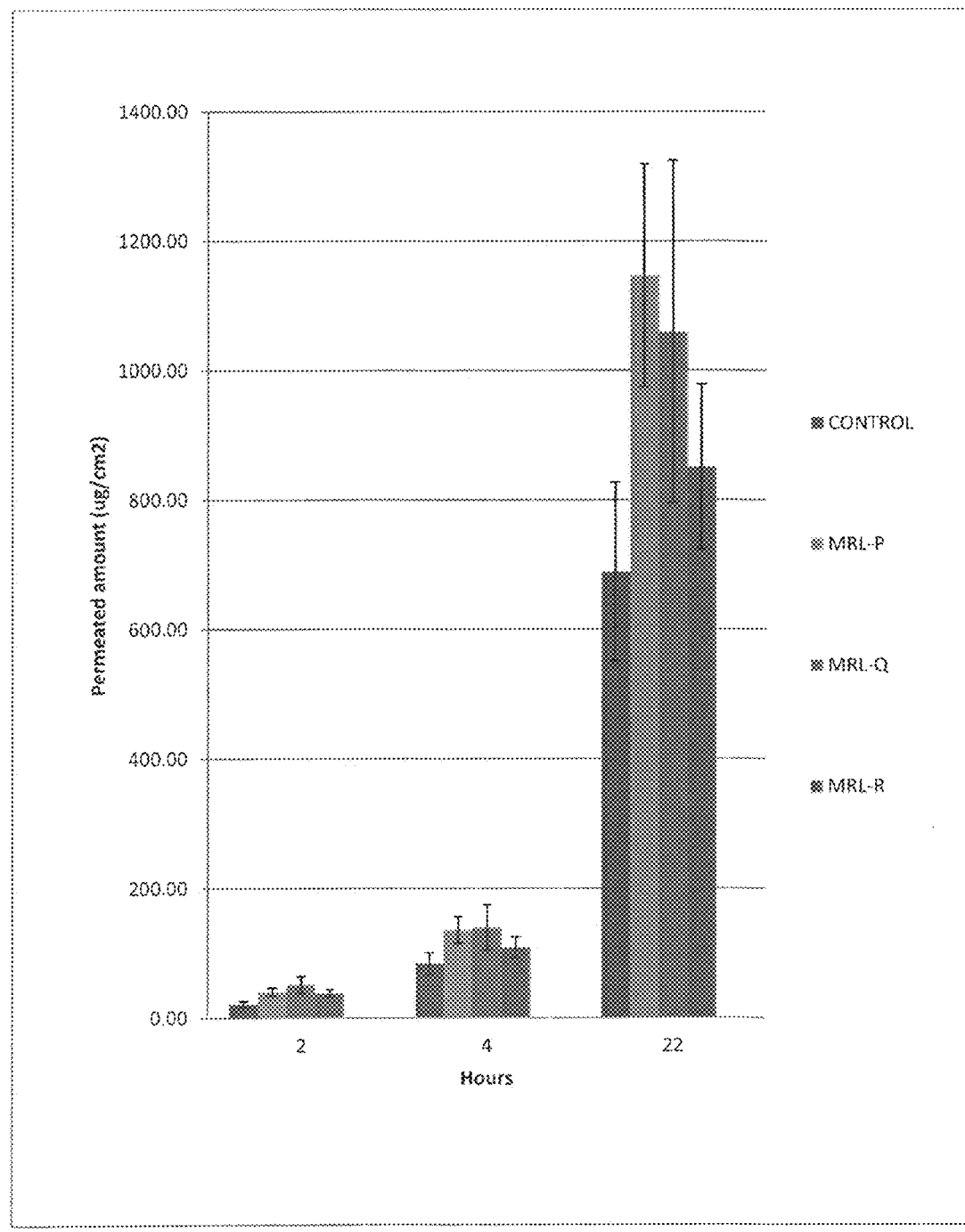
FIG. 8 is a histogram showing amount of ketoprofen permeated two hours, four hours, and 22 hours after application of compositions shown in Table 8.

The permeation results are shown in FIG. 8. The results indicate that the combination of a cross-linked polyacrylic acid interpolymer and a cross-linked polyacrylic acid homopolymer provides improved permeation of ketoprofen as compared to homopolymer only as the thickening agent.

II. Freeze/Thaw Stability.

1. Freeze/Thaw Stability Study was Conducted on Compositions Containing Different Ratios of Carbopol® 980 to Carbopol® Ultrez 10.

a. Freeze-Thaw results in compositions containing Carbopol® 980 only.

TABLE 9

| | Composition (% w/w) | | | |
|---|---|---|---|---|
| | Ketoprofen | Oxybenzone | BSA (Whey) | Polymer |
| MRL-S | 2.5 | Yes | No | Carbopol ® 980 |
| Control | 5 | No | No | Carbopol ® 980 |
| MRL-T | 5 | Yes | Yes | Carbopol ® 980 |
| MRL-U | 5 | No | No | Carbopol ® 980 |

TABLE 9-continued

| | Composition (% w/w) | | | |
|---|---|---|---|---|
| | Ketoprofen | Oxybenzone | BSA (Whey) | Polymer |
| MRL-V | 10 | No | No | Carbopol ® 980 |
| MRL-W | 5 | Yes | Whey | Carbopol ® 980 |

Figure 9:
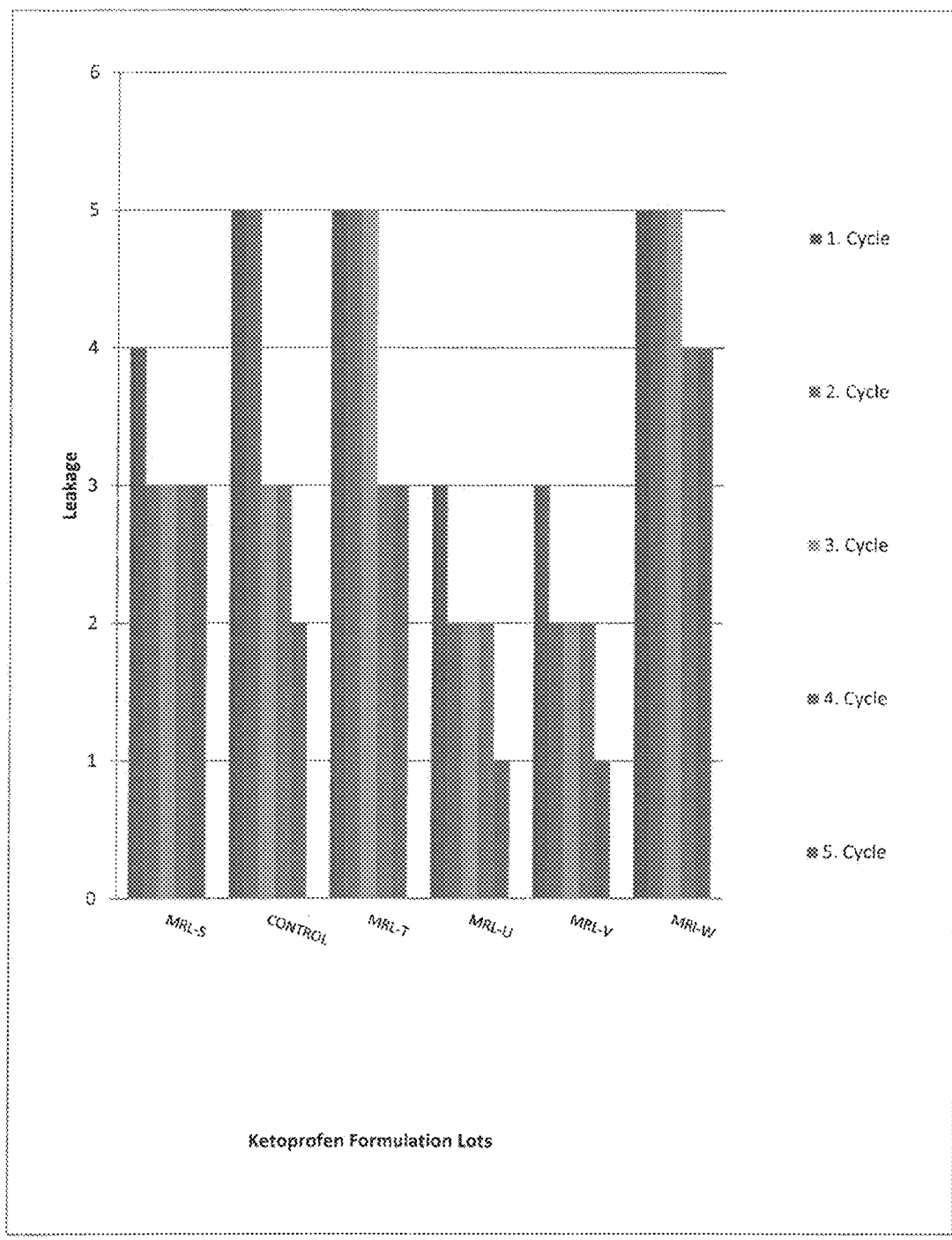
FIG. 9 is a histogram showing freeze-thaw behaviour of the compositions identified in Table 9.

The results are shown in FIG. 9. After three freeze/thaw cycles all preparations exhibited some phase separation.

b. Freeze-Thaw results of compositions containing 5% w/w ketoprofen and various ratios of Carbopol® Ultrez 10/Carbopol® 980 and one formulation containing 10% ketoprofen.

TABLE 10

| | Composition (% w/w) (100 gram batches) | | | |
|---|---|---|---|---|
| | Ketoprofen | Oxybenzone | BSA (Whey) | Polymer |
| MRL-A | 5 | Yes | No | Ultrez 10 |
| MRL-B | 5 | Yes | No | Ultrez 20 |
| MRL-C | 5 | Yes | No | Carbopol ® 980 = 1, Ultrez 10 = 0.75 |
| MRL-D | 5 | Yes | No | Carbopol ® 980 = 1, Ultrez 20 = 0.75 |
| MRL-F | 10 | Yes | No | Carbopol ® 980 = 1.5, Ultrez 10 = 0.25 |

Figure 10:
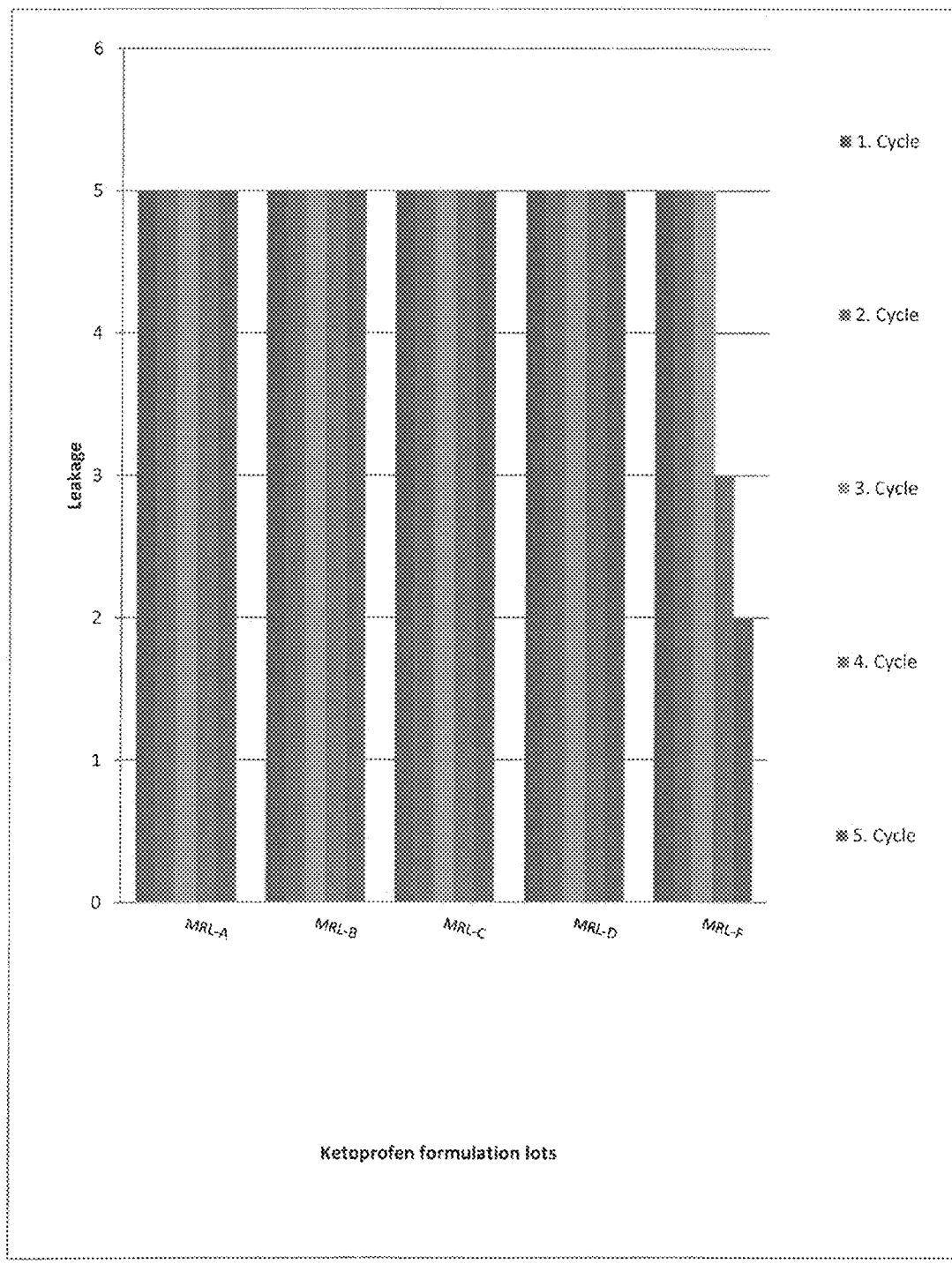
FIG. 10 is a histogram showing freeze-thaw behaviour of the compositions identified in Table 10.

Carbopol® Ultrez 10 and combinations thereof with Carbopol® 980 showed some resistance to phase separation. With the 10% ketoprofen composition containing 025% Carbopol® Ultrez 10, phase separation after 3 cycles was observed. The results are shown in FIG. 10.

c. Freeze-Thaw results of formulations containing 10% w/w ketoprofen and either Carbopol® 980 at 1.75% or Carbopol® 980 at 1.5% plus Carbopol® Ultrez 10 at 0.25% and one formulation containing 0% ketoprofen (control formula).

TABLE 11

| | Composition (% w/w) (1 kg batches) | | | |
|---|---|---|---|---|
| | Ketoprofen | Oxy-benzone | BSA (Whey) | Polymer |
| MRL-X | 10 | 5 | No | Carbopol ® 980 = 1.75 |
| MRL-Y | 0 | 5 | No | Carbopol ® 980 = 1.5, Carbopol ® Ultrez 10 = 0.25 |
| MRL-E | 10 | 5 | No | Carbopol ® Ultrez 10 = 1.75 |

Figure 11:
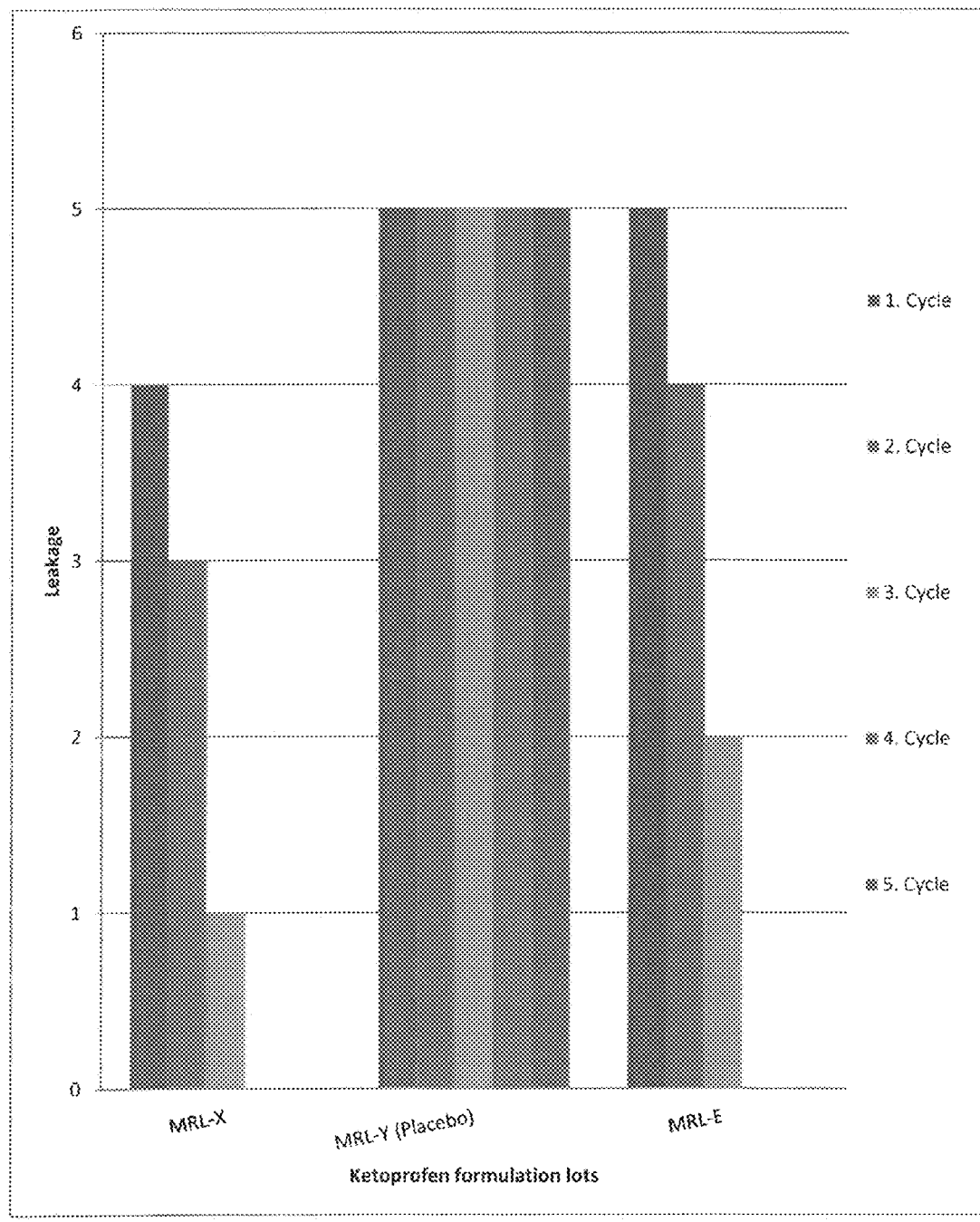
FIG. 11 is a histogram showing freeze-thaw behaviour of the compositions identified in Table 11.

The control compositions showed no leakage after 5 cycles. The Carbopol® Ultrez 10 only composition and the Carbopol® 980 only composition failed after two cycles. The Carbopol® Ultrez 10 only composition had a better appearance than the Carbopol® 980 only composition. The results are shown in FIG. 11.

d. Freeze-Thaw results of formulations containing 10% w/w ketoprofen and various ratios of Carbopol® 980 and Carbopol® Ultrez 10.

TABLE 12

| | Composition (% w/w) (100 gram batches) | | | |
|---|---|---|---|---|
| | Ketoprofen | Oxybenzone | BSA | Polymer |
| MRL-E | 10 | 5 | No | Ultrez 10 = 1.75 |
| MRL-G | 10 | 5 | No | Carbopol ® 980 = 1.0, Ultrez 10 = 0.75 |

TABLE 12-continued

| | Composition (% w/w) (100 gram batches) | | | |
|---|---|---|---|---|
| | Ketoprofen | Oxybenzone | BSA | Polymer |
| MRL-H | 10 | 5 | No | Carbopol ® 980 = 1.25 Ultrez 10 = 0.5 |
| MRL-K | 10 | 5 | No | Carbopol ® 980 = 1 Ultrez 10 = 0.75 |

Figure 12:
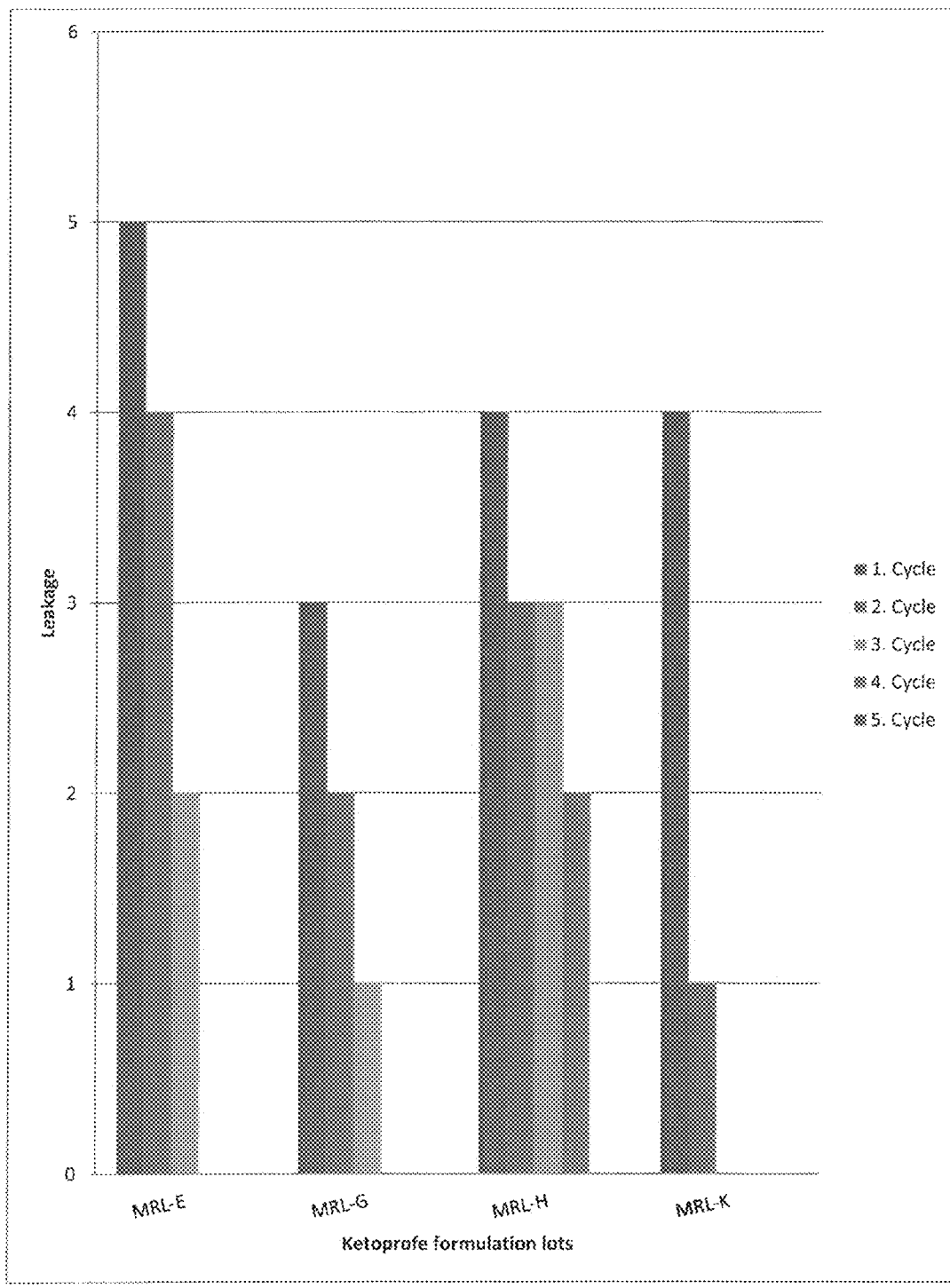
FIG. 12 is a histogram showing freeze-thaw behaviour of the compositions identified in Table 12.

Compositions with relatively lower interpolymer/homopolymer weight ratios exhibited higher phase separation. The results are shown in FIG. 12.

e. Freeze-Thaw results of compositions containing 10% w/w ketoprofen, Carbopol® 980 and Carbopol® Ultrez 10 but with lower Carbopol® 980 content.

TABLE 13

| | Composition (% w/w) (100 gram batches) | | | |
|---|---|---|---|---|
| | Ketoprofen | Oxybenzone | BSA | Polymer |
| MRL-Z | 10 | 5 | No | Carbopol ® 980 = 0.75, Carbopol ® Ultrez 10 = 1.0 |
| MRL-L | 10 | 5 | No | Carbopol ® 980 = 0.5, Carbopol ® Ultrez 10 = 1.25 |
| MRL-M | 10 | 5 | No | Carbopol ® 980 = 0.25 Carbopol ® Ultrez 10 = 1.5 |

Figure 13:
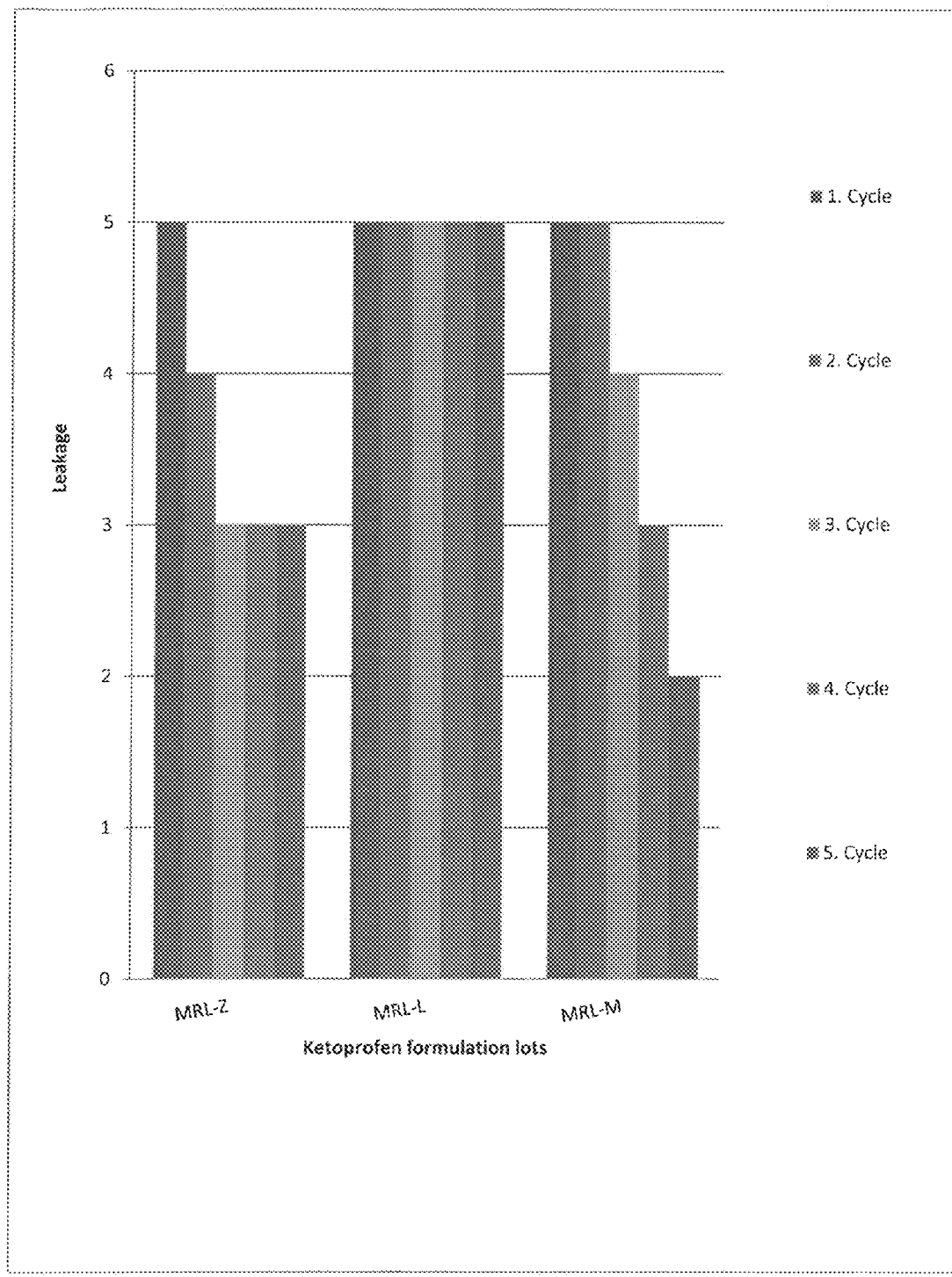
FIG. 13 is a histogram showing freeze-thaw behaviour of the compositions identified in Table 13.

No phase separation was observed at interpolymer/homopolymer weight ratio of 2.5:1 after five freeze/thaw cycles. The results are shown in FIG. 13.

f. Freeze-Thaw results of compositions containing 10% w/w ketoprofen and various ratios for Carbopol® 980/Ultrez 10 but with lower amounts of alcohol.

TABLE 14

| | Composition (% w/w) | | | |
|---|---|---|---|---|
| | Ketoprofen | Oxybenzone | BSA | Polymer |
| MRL-AA | 10 | 5 | No | Carbopol ® 980 = 0.5, Carbopol ® Ultrez 10 = 1.5, EtOH = 10 |
| MRL-P | 10 | 5 | No | Carbopol ® 980 = 0.75, Carbopol ® Ultrez 10 = 1.25, EtOH = 10 |
| MRL-AB | 10 | 5 | No | Carbopol ® 980 = 0.5, Carbopol ® Ultrez 10 = 1.25, Alcohols = 8 + 8 + 8 |
| MRL-Q | 10 | 5 | No | Carbopol ® 980 = 0.5, Carbopol ® Ultrez 10 = 1.25, EtOH = 15 |
| MRL-R | 10 | 5 | No | Carbopol ® 980 = 0.75, Carbopol ® Ultrez 10 = 1.25, EtOH = 15 |

Figure 14:
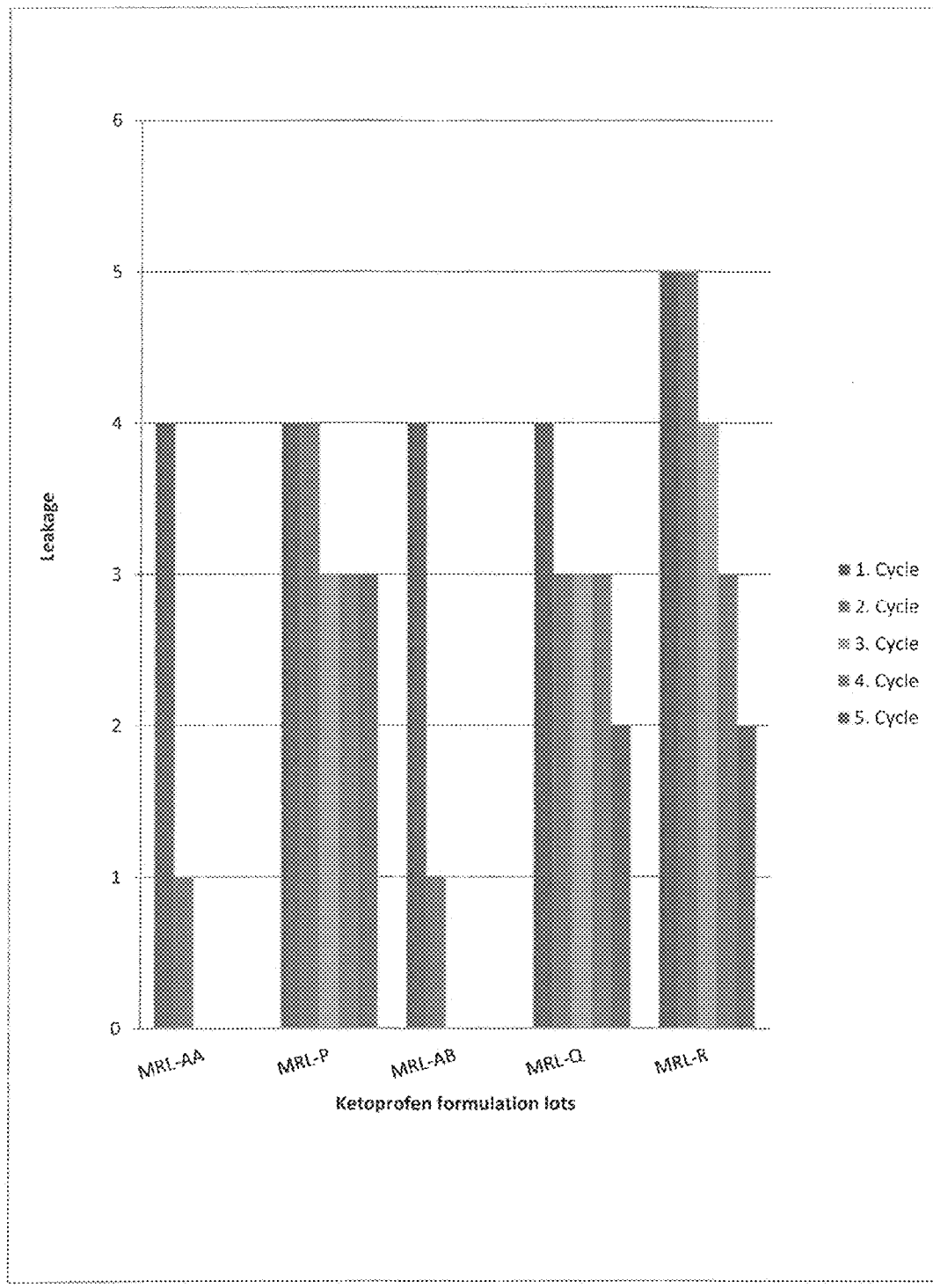
FIG. 14 is a histogram showing freeze-thaw behaviour of the compositions identified in Table 14.

The higher polymer levels and various alcohol levels exhibited phase separation in the freeze/thaw studies, even though they look esthetically appealing at normal room temperature conditions. The most freeze/thaw resistant formulation of this group contained 1.25% Carbopol® Ultrez 10, 0.75% Carbopol® 980 and 15% ethanol. The results are shown in FIG. 14.

III. Stability of Compositions 1. 3-Month Stability—5% w/w Ketoprofen—1 kg Batch

TABLE 15

| Composition (% w/w) | |
|---|---|
| Ingredient | MRL-U |
| Ketoprofen | 5 |
| Carbopol ® 980 NF | 2 |
| Deionized Water | 57.23 |
| Disodium EDTA | 0.05 |
| Methylparaben | 0.2 |
| Propylparaben | 0.02 |
| Isopropyl Myristate, NF | 5 |
| Ethyl Alcohol, USP anh. | 28.5 |
| Triethanolamine | 2 |

Stability at 25° C.

| Time Point | Temperature (° C.) | Ketoprofen % | Recovered % | SD |
|---|---|---|---|---|
| 0 hr. | 25 | 5 | 105.57 | 3.17 |
| 1 month | 25 | 5 | 112.18 | 1.79 |
| 2 month | 25 | 5 | 106.15 | 2.74 |
| 3 month | 25 | 5 | 108.75 | 2.83 |

Stability at 40° C.

| Time Point | Temperature (° C.) | Ketoprofen % | Recovered % | SD |
|---|---|---|---|---|
| 0 hr. | 25 | 5 | 105.57 | 3.17 |
| 1 month | 40 | 5 | 112.71 | 4.61 |
| 2 month | 40 | 5 | 110.2 | 2.01 |
| 3 month | 40 | 5 | 102.77 | 4.19 |

Photo Stability at 25° C.

| Time Point | Temperature (° C.) | Ketoprofen % | Recovered % | SD |
|---|---|---|---|---|
| 0 hr./photostab | 25 | 5 | 64.99 | 2.82 |
| 1 m/photostab | 25 | 5 | 78.35 | 2.15 |
| 2 m/photostab | 25 | 5 | 64.66 | 1.59 |
| 3 m/photostab | 25 | 5 | 81.02 | 0.59 |

Photo Stability at 40° C.

| Time Point | Temperature (° C.) | Ketoprofen % | Recovered % | SD |
|---|---|---|---|---|
| 0 hr./photostab | 25 | 5 | 64.99 | 2.82 |
| 1 m/photostab | 40 | 5 | 58.17 | 2.02 |
| 2 m/photostab | 40 | 5 | 56.08 | 2.26 |
| 3 m/photostab | 40 | 5 | 62.62 | 0.81 |

This composition, without oxybenzone, is physically and chemically stable for up to 3 months at 40° C.; however, it is not less photostable.

2. 3-Month Stability—10% w/w/Ketoprofen—Kg Batch.

TABLE 16

| Composition (% w/w) | |
|---|---|
| Ingredient | MRL-V |
| Ketoprofen | 10 |
| Carbopol ® 980 NF | 2 |
| Deionized Water | 52.23 |
| Disodium EDTA | 0.05 |
| Methylparaben | 0.2 |
| Propylparaben | 0.02 |
| Isopropyl Myristate, NF | 5 |
| Ethyl Alcohol USP, anh. | 28.5 |
| Triethanolamine | 2 |

Stability at 25° C.

| Time Point | Temperature (° C.) | Ketoprofen % | Recovered % | SD |
|---|---|---|---|---|
| 0 hr. | 25 | 10 | 100.06 | 2.97 |
| 1 month | 25 | 10 | 107.96 | 2.43 |
| 2 month | 25 | 10 | 106.06 | 0.54 |
| 3 month | 25 | 10 | 108.23 | 1.56 |

Stability at 40° C.

| Time Point | Temperature (° C.) | Ketoprofen % | Recovered % | SD |
|---|---|---|---|---|
| 0 hr. | 25 | 10 | 100.06 | 2.97 |
| 1 month | 40 | 10 | 102.04 | 4.69 |
| 2 month | 40 | 10 | 96.29 | 15.03 |
| 3 month | 40 | 10 | 92.15 | 9.83 |

Photo Stability at 25° C.

| Time Point | Temperature (° C.) | Ketoprofen % | Recovered % | SD |
|---|---|---|---|---|
| 0 hr./photostab | 25 | 10 | 69.58 | 1.31 |
| 1 m/photostab | 25 | 10 | 87.39 | 2.69 |
| 2 m/photostab | 25 | 10 | 73.46 | 0.9 |
| 3 m/photostab | 25 | 10 | 94.87 | 1.49 |

Photo Stability at 40° C.

| Time Point | Temperature (° C.) | Ketoprofen % | Recovered % | SD |
|---|---|---|---|---|
| 0 hr./photostab | 25 | 10 | 69.58 | 1.31 |
| 1 m/photostab | 40 | 10 | 63.8 | 3.08 |
| 2 m/photostab | 40 | 10 | 57.79 | 1.99 |
| 3 m/photostab | 40 | 10 | 56.15 | 7.98 |

Composition containing 10% ketoprofen, without oxybenzone and antioxidants, shows approximately 8% degradation of ketoprofen after 3 months, at 40° C., and significant photodegradation at all timepoints.

3. 3-Month Stability—5% w/w Ketoprofen with 5% Oxybenzone and 2% BSA.

TABLE 17

| Composition (% w/w) | |
|---|---|
| Ingredient | MRL-T |
| Ketoprofen | 5 |
| Carbopol ® 980 NF | 1.75 |
| Deionized Water | 49.48 |
| Disodium EDTA | 0.05 |
| Methylparaben, NF | 0.2 |
| Propylparaben, NF | 0.02 |
| Propylene glycol | 10 |
| Isopropanol | 10 |
| Cremophor 40[1] | 0.5 |
| Bovine serum albumin | 2 |
| Oxybenzone | 5 |
| BHT | 1 |
| Vitamin E | 0.5 |
| Isopropyl Myristate | 3 |
| Ethyl Alcohol USP, anh. | 10 |
| Triethanolamine, NF | 1.5 |

[1]PEG 40 to Hydrogenated Castor Oil.

Stability at 25° C.

| Time Point | Temperature (° C.) | Ketoprofen % | Recovered % | SD | Oxybenzone % | Recovered % | SD |
|---|---|---|---|---|---|---|---|
| 0 hr. | 25 | 5 | 106.58 | 3.85 | 5 | 102.85 | 3.35 |
| 1 month | 25 | 5 | 106.41 | 2.65 | 5 | 103.85 | 2.66 |
| 2 month | 25 | 5 | 103.89 | 1.77 | 5 | 103.25 | 0.78 |
| 3 month | 25 | 5 | 101.06 | 1.24 | 5 | 100.69 | 2.09 |

Stability at 40° C.

| Time Point | Temperature (° C.) | Ketoprofen % | Recovered % | SD | Oxybenzone % | Recovered % | SD |
|---|---|---|---|---|---|---|---|
| 0 hr. | 25 | 5 | 106.58 | 3.85 | 5 | 102.85 | 3.35 |
| 1 month | 40 | 5 | 108.84 | 1.7 | 5 | 108.95 | 3.38 |
| 2 month | 40 | 5 | 105.00 | 1.27 | 5 | 107.25 | 0.78 |
| 3 month | 40 | 5 | 93.38 | 0.86 | 5 | 105.67 | 0.58 |

Photo Stability at 25° C.

| Time Point | Temperature (° C.) | Ketoprofen % | Recovered % | SD | Oxybenzone % | Recovered % | SD |
|---|---|---|---|---|---|---|---|
| 0 hr./photostab | 25 | 5 | 101.08 | 0.26 | 5 | 101.43 | 0.8 |
| 1 m/photostab | 25 | 5 | 101.93 | 2.51 | 5 | 104.25 | 1.07 |
| 2 m/photostab | 25 | 5 | 97.01 | 1.79 | 5 | 97.97 | 2.46 |
| 3 m/photostab | 25 | 5 | 98.00 | 0.38 | 5 | 105.02 | 0.65 |

Photo Stability at 40° C.

| Time Point | Temperature (° C.) | Ketoprofen % | Recovered % | SD | Oxybenzone % | Recovered % | SD |
|---|---|---|---|---|---|---|---|
| 0 hr./photostab | 25 | 5 | 101.08 | 0.26 | 5 | 101.43 | 0.8 |
| 1 m/photostab | 40 | 5 | 94.85 | 0.35 | 5 | 102.95 | 1.2 |
| 2 m/photostab | 40 | 5 | 92.80 | 2.47 | 5 | 95.04 | 4.09 |
| 3 m/photostab | 40 | 5 | 91.39 | 1.27 | 5 | 101.9 | 2.23 |

This composition was chemically stable after 3 months 25° C. and 40° C. Photodegradation was seen with samples stored at 40° C. but recovery was still above 90% after 3 months.

4. 3-Month Stability—5% w/w Ketoprofen with 5% Oxybenzone and 2% Soy Protein.

TABLE 18

| Composition (% w/w) | |
|---|---|
| Ingredient | MRL-AC |
| Ketoprofen | 5 |
| Carbopol ® 981 | 1.75 |
| Deionized Water | 49.48 |
| Disodium EDTA | 0.05 |
| Methylparaben, NF | 0.2 |
| Propylparaben, NF | 0.02 |
| Propylene glycol | 10 |
| Isopropanol | 10 |
| Cremophor 40[1] | 0.5 |
| Soy protein | 2 |
| Oxybenzone | 5 |
| BHT | 1 |
| Vitamin E | 0.5 |
| Isopropyl Myristate | 3 |
| Ethyl Alcohol USP | 10 |
| Triethanolamine, NF | 1.5 |

[1]Peg-40 Hydrogenated Castor Oil.

Stability at 25° C.

| Time Point | Temperature (° C.) | Ketoprofen % | Recovered % | SD | Oxybenzone % | Recovered % | SD |
|---|---|---|---|---|---|---|---|
| 0 hr. | 25 | 5 | 104.01 | 1.29 | 5 | 100.48 | 2.33 |
| 1 month | 25 | 5 | 107.53 | 1.73 | 5 | 103.65 | 1.72 |
| 2 month | 25 | 5 | 103.24 | 0.41 | 5 | 103.55 | 2.26 |
| 3 month | 25 | 5 | 105.27 | 2.59 | 5 | 109.35 | 0.49 |

Stability at 40° C.

| Time Point | Temperature (° C.) | Ketoprofen % | Recovered % | SD | Oxybenzone % | Recovered % | SD |
|---|---|---|---|---|---|---|---|
| 0 hr. | 25 | 5 | 104.01 | 1.29 | 5 | 100.48 | 2.33 |
| 1 month | 40 | 5 | 106.54 | 1.25 | 5 | 106.19 | 2.03 |
| 2 month | 40 | 5 | 101.37 | 1 | 5 | 103.63 | 1.74 |
| 3 month | 40 | 5 | 99.87 | 1.93 | 5 | 108.08 | 2.67 |

Photo Stability at 25° C.

| Time Point | Temperature (° C.) | Ketoprofen % | Recovered % | SD | Oxybenzone % | Recovered % | SD |
|---|---|---|---|---|---|---|---|
| 0 hr./photostab | 25 | 5 | 99.27 | 0.9 | 5 | 101.01 | 2.17 |
| 1 m/photostab | 25 | 5 | 106.17 | 4.65 | 5 | 102.15 | 0.21 |

-continued

| Time Point | Temperature (° C.) | Ketoprofen % | Recovered % | SD | Oxybenzone % | Recovered % | SD |
|---|---|---|---|---|---|---|---|
| 2 m/photostab | 25 | 5 | 96.27 | 1.36 | 5 | 99.55 | 1.15 |
| 3 m/photostab | 25 | 5 | 97.14 | 1.59 | 5 | 100.07 | 1.88 |

Photo Stability at 40° C.

| Time Point | Temperature (° C.) | Ketoprofen % | Recovered % | SD | Oxybenzone % | Recovered % | SD |
|---|---|---|---|---|---|---|---|
| 0 hr./photostab | 25 | 5 | 99.27 | 0.9 | 5 | 101.01 | 2.17 |
| 1 m/photostab | 40 | 5 | 94.25 | 3.75 | 5 | 101.6 | 1.7 |
| 2 m/photostab | 40 | 5 | 93.46 | 0.17 | 5 | 100.37 | 0.61 |
| 3 m/photostab | 40 | 5 | 92.21 | 0.84 | 5 | 101.69 | 1/−7 |

Preparation was chemically stable after 3 months 25° C. and 40° C. Photodegradation was seen when samples stored at 40° C. but ketoprofen recovery still above 90% after three months.

The foregoing compositions are oil-in-water emulsions having a cream-like consistency and are useful for alleviating pain due to migraine when administered to provide ketoprofen in an amount up to about 500 mg per daily dose.

The present compositions are particularly well suited for treating pain associated with a headache such as migraine, trigeminal autonomic cephalgia, headache caused by a vascular condition, and the like. Preferably, a therapeutically effective amount of the present, ketoprofen-containing composition is administered at a site along the orbital foramen, the base of the auricolo-temporal branch of the trigeminal nerve, the auricolo-temporal branch of the greater occipital nerve, the postauricular region intravasal trigeminal nerve endings, the nasal parasympathetic nerve endings, or a combination thereof.

The present compositions are also well suited for treatment of joint pain, muscle pain, peripheral neuropathy, asteoarthritic pain, chronic lower back pain, inflammatory pain, orthopedic injury pain, Reflex Sympathetic Dystrophy (RSD), peripheral neuritis, fibromyalgia, diabetic neuropathy and the like.

The term "therapeutically effective amount" as used herein and the appended claims means an amount of the present composition that provides an amount of ketoprofen sufficient to have a therapeutic benefit in relieving pain. Typically such an amount is in the range of about 100 milligrams to about 300 milligrams of ketoprofen per application.

The foregoing description is intended as illustrative, and is not to be taken as limiting. Still other variants within the spirit and scope of the present invention are possible and will readily present themselves to those skilled in the art.

We claim:

1. A topical composition which is an oil-in-water emulsion and comprises, on a weight basis:
   about 0.5 to about 15 percent ketoprofen, about 0.01 to about 1 percent of a chelating agent, about 0.15 to about 1.5 percent of a cross-linked polyacrylic acid interpolymer, about 0.15 to about 1.5 percent of a cross-linked polyacrylic acid homopolymer, about 2.5 to about 6 percent oxybenzone, about 0.25 to about 2.5 percent of a an emulsifying agent, about 5 to about 15 percent of a water-miscible alkylene glycol, about 10 to about 30 percent of a $C_2$ to $C_3$ alkanol, about 0.5 to about 2.5 percent of a cosmetic preservative, about 0.02 to about 2 percent of an antioxidant, about 0.001 to about 0.1 percent of an emollient, a pH modifier in an amount sufficient to maintain a pH value of the composition in the range of about 4.5 to about 6, and the remainder water.

2. The topical composition in accordance with claim 1 wherein the oil-in-water emulsion has a cream-like consistency.

3. The topical composition in accordance with claim 1 and comprising:
   about 10 percent ketoprofen, about 0.05 percent disodium salt of ethylenediaminetetracetic acid, about 1.25 percent of a cross-linked polyacrylic acid interpolymer, about 0.5 percent of a cross-linked polyacrylic acid homopolymer, about 5 percent of oxybenzone, about 0.5 percent of PEG-40 hydrogenated castor oil, about 10 percent propylene glycol, about 10 percent of anhydrous ethanol, about 9 percent isopropanol, about 1 percent benzyl alcohol, about 0.05 percent Vitamin E, about 1 percent of butylated hydroxytoluene, about 3 percent isopropyl myristate, about 1.5 percent triethanolamine, and the rest water.

4. The topical composition in accordance with claim 1 and comprising:
   about 5 percent ketoprofen, about 0.05 percent disodium salt of ethylenediaminetetracetic acid, about 1.25 percent of a cross-linked polyacrylic acid interpolymer, about 0.5 percent of a cross-linked polyacrylic acid homopolymer, about 5 percent of oxybenzone, about 0.5 percent of PEG-40 hydrogenated castor oil, about 10 percent propylene glycol, about 10 percent of anhydrous ethanol, about 9 percent isopropanol, about 1 percent benzyl alcohol, about 0.05 percent Vitamin E, about 1 percent of butylated hydroxytoluene, about 3 percent isopropyl myristate, about 1.5 percent triethanolamine, and the rest water.

5. The topical composition in accordance with claim 1 and comprising:
   about 0.5 percent ketoprofen, about 0.05 percent disodium salt of ethylenediaminetetracetic acid, about 1.25 percent of a cross-linked polyacrylic acid interpolymer, about 0.5 percent of a cross-linked polyacrylic acid homopolymer, about 5 percent of oxybenzone, about 0.5 percent of PEG-40 hydrogenated castor oil, about 10 percent propylene glycol, about 10 percent of anhydrous ethanol, about 9 percent isopropanol, about 1 percent benzyl alcohol, about 0.05 percent Vitamin E, about 1 percent of butylated hydroxytoluene, about 3 percent isopropyl myristate, about 1.5 percent triethanolamine, and the rest water.

6. A method of treating pain which comprises topical application of a therapeutically effective amount of the composition of claim 1 to the patient suffering from pain.

7. The method in accordance with claim 6 wherein the composition is applied in an amount providing up to about 500 milligrams of ketoprofen per application.

8. The method in accordance with claim 6 wherein the composition is applied daily.

9. A method of treating migraine which comprises topical application of a therapeutically effective amount of the composition of claim 1 to the forehead of a patient suffering from migraine.

10. The method in accordance with claim 9 wherein the composition is applied daily.

* * * * *